United States Patent
Phaneuf et al.

(10) Patent No.: US 6,453,063 B1
(45) Date of Patent: Sep. 17, 2002

(54) AUTOMATIC FOCUSED ION BEAM IMAGING SYSTEM AND METHOD

(75) Inventors: Michael Phaneuf, Ottawa; Dick James, Carp; Julia Elvidge, Ottawa; Pierrette Breton, Stittsville; Terry Ludlow, Ottawa; David Skoll, Ottawa; Bryan Socransky, Ottawa, all of (CA); Louise Weaver, Nijmegen (NL); Ray Haythornthwaite, Nepean (CA)

(73) Assignee: Chipworks, Ottawa (CA)

( * ) Notice: Subject to any disclaimer, the term of this patent is extended or adjusted under 35 U.S.C. 154(b) by 0 days.

(21) Appl. No.: 09/238,435

(22) Filed: Jan. 28, 1999

Related U.S. Application Data

(60) Provisional application No. 60/072,873, filed on Jan. 28, 1998.

(51) Int. Cl.$^7$ .......................... G06K 9/00; G01N 23/00
(52) U.S. Cl. ........................ 382/145; 250/309
(58) Field of Search ................ 382/145, 147, 382/151, 144, 141, 146, 149, 150, 154, 181, 216, 255, 254, 284; 250/309, 311

(56) References Cited

U.S. PATENT DOCUMENTS

| | | | |
|---|---|---|---|
| 4,553,260 A | 11/1985 | Belt et al. ................. | 382/22 |
| 4,623,255 A | 11/1986 | Suszko ..................... | 356/389 |
| 4,639,301 A | 1/1987 | Doherty et al. .......... | 204/192.31 |
| 4,673,101 A | 6/1987 | Guarino et al. .......... | 220/335 |

(List continued on next page.)

FOREIGN PATENT DOCUMENTS

| | | | |
|---|---|---|---|
| CA | 2168328 | 1/1996 | ............ G06T/7/60 |
| CA | 2216900 | 9/1997 | ............ G06T/7/60 |

OTHER PUBLICATIONS

T.O. Kiang and E.M. Hwa, "Extracting Layers from Optical Images of Silicon Integrated Circuit Chips," pp. 571–575.

O.K. Tan, M.H. Er, Y.W. Chow, W.S. Chow, "An Automatic Layer Extractor of IC Chips," pp. 1346–1349.

C.C. Jong, O.K. Tan, S.C. Sing., M.L.J.Siow, "Geometrical figure processing for IC layout extracted from silicon die image," Int. J. Electronics, 1995, vol. 78, No. 2, pp. 367–394.

Jong et al. "Computer–aided Reconstruction of IC Layout from Image–based representation" Proceedings of the 5$^{th}$ International Symposium on IC Technology System and Applications pp 446–469, Sep. 1993.

(List continued on next page.)

*Primary Examiner*—Leo Boudreau
*Assistant Examiner*—Kanji Patel
(74) *Attorney, Agent, or Firm*—Max R. Wood; Ogilvy Renault

(57) ABSTRACT

A method of imaging an integrated circuit using a focused ion beam system is presented. According to the method an integrated circuit is imaged in plan-view using a focused ion beam system. Circuit information is then extracted absent processing. In another embodiment, a method and system for imaging an entire IC automatically without removing the IC from the imaging system and requiring minimal operator intervention is presented. The method employs a focused ion beam system to image an exposed layer of an integrated circuit and then to etch a portion of the exposed layer in situ. Imaging and etching are repeated until substantially the entire integrated circuit is imaged. A processor is used to assemble the layers into a three-dimensional topography of the integrated circuit. Because of known relationships between layers, the mosaicing is facilitated and the final topography is more reliable than those produced by currently known computer implemented methods.

23 Claims, 8 Drawing Sheets

U.S. PATENT DOCUMENTS

| | | | |
|---|---|---|---|
| 4,699,555 A | 10/1987 | Guarino | 414/217 |
| 4,711,438 A | 12/1987 | Guarino | 269/152 |
| 4,748,675 A | 5/1988 | Suzuki et al. | 382/21 |
| 4,766,516 A | 8/1988 | Ozdemir et al. | 361/380 |
| 4,777,372 A | 10/1988 | Guarino | 250/442.1 |
| 4,783,829 A | 11/1988 | Miyakawa et al. | 382/22 |
| 4,791,586 A | 12/1988 | Maeda et al. | 364/491 |
| 4,874,947 A | 10/1989 | Ward et al. | 250/309 |
| 4,943,732 A | 7/1990 | Economou | 250/572 |
| 4,976,843 A | 12/1990 | Ward et al. | 204/298.36 |
| 5,034,612 A | 7/1991 | Ward et al. | 250/423 R |
| 5,050,222 A | 9/1991 | Lee | 382/21 |
| 5,086,477 A | 2/1992 | Yu et al. | 382/8 |
| 5,103,102 A | 4/1992 | Economou et al. | 250/492.2 |
| 5,155,368 A | 10/1992 | Edwards, Jr. et al. | 250/396 R |
| 5,163,005 A | 11/1992 | Greene et al. | 364/468 |
| 5,187,754 A | 2/1993 | Currin et al. | 382/54 |
| 5,188,705 A | 2/1993 | Swanson et al. | 156/643 |
| 5,191,213 A | 3/1993 | Ahmed et al. | 250/310 |
| 5,199,159 A | 4/1993 | Waldsmith | 29/596 |
| 5,214,718 A | 5/1993 | Khosla | 382/22 |
| 5,241,182 A | 8/1993 | Martin et al. | 250/396 R |
| 5,329,162 A | 7/1994 | Nadaoka | 257/774 |
| 5,335,298 A | 8/1994 | Hevenor et al. | 382/54 |
| 5,376,791 A | 12/1994 | Swanson et al. | 250/309 |
| 5,392,222 A | 2/1995 | Noble | 364/490 |
| 5,399,441 A | 3/1995 | Bearinger et al. | 428/689 |
| 5,435,850 A | 7/1995 | Rasmussen | 118/726 |
| 5,502,306 A | 3/1996 | Meisburger et al. | 250/310 |
| 5,541,411 A | 7/1996 | Lindquist et al. | 250/309 |
| 5,559,718 A | 9/1996 | Baisuck et al. | 364/491 |
| 5,561,293 A | 10/1996 | Peng et al. | 250/307 |
| 5,578,821 A | 11/1996 | Meisberger et al. | 250/310 |
| 5,694,481 A | 12/1997 | Lam et al. | 382/145 |
| 5,776,645 A * | 7/1998 | Barr et al. | 430/22 |

OTHER PUBLICATIONS

Tan et al. "Integrated Circuit Chip Layer Analysis" Proceedings of the 5$^{th}$ International Symposium on IC Technology System and Applications pp 461–465, Sep. 1993.

Welcome to Philips Electroscan, http://www.electroscan.com/ "Ion Beams in Focus," European Semiconductor, Mar. 1996, pp. 49–50.

* cited by examiner

AUTOMATIC FOCUSED ION BEAM IMAGING SYSTEM AND METHOD

This application is a continuation of U.S. Provisional application no. 60/072,873 filed on Jan. 28, 1998.

FIELD OF THE INVENTION

The invention relates to integrated circuit imaging and analysis and more particularly to the use of focused ion beams for imaging integrated circuits.

BACKGROUND OF THE INVENTION

In the past, reverse engineering of circuits was a straightforward task. A circuit board was examined for traces providing a series of conductive connections between components. Circuit components were then analysed to determine connected elements and finally, a schematic of the board was entered for improvement, re-layout, or incorporation into a current design.

With the advent of MSI, LSI, and VLSI, this process became far more tedious. Initial attempts at reverse engineering integrated circuits relied on visual images of integrated circuit layers. Overlapping portions of a layer of an integrated circuit were photographed such that a portion of a layer is photographed. The images were developed as photographs and the photographs were assembled by hand in order to overlap adjacent images appropriately. Because of the redundant nature of integrated circuits, assembling the overlapping images into a single large composite image was difficult and required some skill.

Once a composite image was formed by taping or gluing the photographs together in an appropriate fashion, analysis of the images began. The analysis was performed by a person skilled in the art of reverse engineering or integrated circuit fault analysis and includes the steps of determining conductors, transistors, capacitors, resistors, etc. and forming a schematic of the circuit in dependence upon the analysis.

Reverse engineering a complex integrated circuit often represents many man months of effort and requires significant contribution by highly skilled individuals.

With the miniaturisation of integrated circuits, optical wavelengths become less useful for imaging. Current state of the art integrated circuit fabrication facilities work at 0.25–0.35 microns and are expected to be further miniaturised. At sizes smaller than these, optical wavelengths become too large to properly image integrated circuit components. In order to overcome this limitation, it has been proposed to use scanning electron microscope (SEM) devices; however, with the use of scanning electron microscopes, new problems arise. Optical imaging captures information of the outermost opaque surface and optical transmission presents certain known problems. SEM devices image only surface information unless materials of different average atomic number are present within the electron beam penetration depth. The topography that is imaged is the final result of all the processes that produce changes in height at the surface such as oxidation and metallization crossovers. Thus it is difficult to extract information unambiguously relating solely to the upper metallization.

It is therefore common to produce images containing a lot of background information as well as an image of an outermost layer. Many current imaging techniques for reverse engineering focus heavily on techniques for processing the information to extract foreground information for circuit analysis. At present, human analysis is the most effective.

It would be advantageous to automate some of the functions required to reverse engineer or analyse an integrated circuit (IC).

Prior Art

In U.S. Pat. No. 4,623,255 in the name of Suszko and issued on Nov. 18, 1986, a Method of Examining Microcircuit Patterns is disclosed. The method comprises the steps of photographing a portion of an IC with dark field illumination and then developing the photograph. As described above, the mosaic formed by assembling photographs is time consuming and requires expertise.

In U.S. Pat. No. 5,086,477 in the name of Yu et al. and issued on Feb. 4, 1992, an Automated System for Extracting Design and Layout Information from an Integrated Circuit is disclosed. The system comprises an image capture means for capturing a plurality of images of an IC and a computer for assembling the images into a large mosaic by determining image overlap or by extrapolating images to fill gaps between adjacent images. Unfortunately, when working with current IC tolerances, gaps between abutting images may contain important circuit elements. Further the system taught by Yu et al. requires a known element to occur on each of several layers in order to align image composites for a multi-layer IC. A skilled worker identifies the known element. Finding and identifying such an element on each layer of the IC is often time consuming. Also, removing an IC from the imaging system in order to prepare it for imaging successive layers, makes aligning successive layers automatically very difficult.

In U.S. Pat. No. 5,191,213 in the name of Ahmed et al. and issued on Mar. 2, 1993, an Integrated Circuit Structure Analysis method and apparatus are disclosed. An electron beam is directed toward successive layers of an IC. Some known problems with the use of electron beam scanning of IC layers are solved by Ahmed et al. Filtering of image data is required to extract foreground data from background data before analysis is possible. This is a significant problem. Also, removing an IC from the imaging system in order to prepare it for imaging successive layers, makes aligning successive layers in an automatic fashion very difficult.

In U.S. Pat. No. 5,694,481 in the name of Lam et al. and issued Dec. 2, 1997, a system for automatically constructing a mosaic of images using polygon extraction and filtering of images is disclosed. The method appears useful for extracting circuit information from SEM image data. The method disclosed deals mostly with the issues of filtering and mosaicing of filtered images. The step of filtering to extract foreground information from background and foreground information is very time consuming because of the size and resolution of the images captured. It would be advantageous to eliminate this step, but unfortunately, using SEM devices automated circuit extraction is not currently possible absent complex filtering of image data.

Focused ion beam (FIB) systems are known for use in several applications. FIBS are useful in micromachining, imaging and etching. The use of FIBS in imaging is well documented. In imaging, an ion beam is focused toward a location and backscattered ions are detected. Other particle emissions caused by collisions between ions within the beam and a surface being imaged are also detected. Analysis of the detected particles results in an image. FIB systems are also used in etching. Etching with FIBS began with applications for cutting traces in integrated circuits to allow for IC repair. With gas assisted etching, FIB systems provide a convenient system for etching away selected material from a surface of an IC in order to form holes of a desired depth.

Gas assisted etching is performed as follows. A reactive gas such as chlorine is fed into the FIBS near a surface of a substrate. The gas adsorbs to the surface approximating a monolayer. When the surface is scanned with ion beams, the energy of the ion beams is used to break chemical bonds, thus causing chemical reactions to proceed. As well as providing the energy needed to break bonds, the ions supply momentum to sputter the substrate. The chemical etching helps to enhance the physical sputtering of the ion beam. Another benefit is that the sputtered particles are volatilised and pumped away by a vacuum system forming part of the FIBS.

Use of correct etchant gas significantly increases etching rate over FIB etching without an etchant gas. The increased etching rate is material dependent so selection of a gas for a particular material results in improved etching performance and improved control because of etching rate decreases when different material is exposed. These two advantages to gas assisted etching are known to allow etching of deep narrow holes.

In U.S. Pat. No. 5,561,293 in the name of Peng et al. and issued on Oct. 1, 1996, a Method of Failure Analysis with CAD Layout Navigation and FIB/SEM Inspection is disclosed. The method incorporates a dual beam scan of a problem area of a failed IC to detect an error in the IC. When no error is detected, layers are etched away to search for the error in other layers. The method disclosed by Peng et al. is applicable to detecting an error in a known or estimated location but on an unknown layer. Examples of errors of this type are hot spots or burns on the IC surface. The general location of the hot spot is known but the heat source depth or differently stated the layer generating the heat is unknown. The method described by Peng et al. is very useful for analysing IC failure. Unfortunately, it is not well suited to reverse engineering because it does not image entire layers within an IC nor does it align different layers within an IC. Further, circuit information extraction from image data is not taught. Using such a disclosure, little regarding reverse engineering of integrated circuits is learned.

Essentially, since a location of the error is known or estimated, the advantage to viewing and etching using a focused ion beam is convenience and time. The disclosure of using the focused ion beam to etch away material, discloses a known technique. The invention directs itself to CAD navigation with error inspection. Unfortunately, due to the fine tolerances in present day ICs, it is impossible to accurately re-align the imaging apparatus for successive layers when, as stated in the disclosure of Peng et al. "the sample is returned to the inspection tool." For the inspection application of Peng et al., the hot spot provides a rough idea as to error location, so exact alignment between layers is inessential. However, for imaging of an entire IC, exact alignment between layers is an important aspect of the reverse engineering process.

In the past, research and expertise has been devoted to filtering images and mosaicing them to form a single composite image of an integrated circuit layer. Unfortunately, the approaches presented heretofore, suffer from significant drawbacks. First, filtering is often imprecise and results in errors, which propagate through to circuit analysis. Second, the time required to filter and mosaic a composite image is extraordinary because of the large amount of images captured of each layer. Third, there is no method for correcting images of poor quality other than recapturing the images using a different sample, which may be difficult to obtain. Fourth, mosaicing of a composite image is not a straightforward task due to stage imprecision, circuit redundancy, and vast areas (when magnified) of unused circuit space. Many other disadvantages of the prior art exist.

The filtering of image data and/or composite images presents the single greatest challenge in the field of automated reverse engineering. It is difficult to extract foreground data from background data in a robust fashion. Also, because of the time requirements, significant delay and cost increases are experienced to analyse each integrated circuit device. Often a small portion of an integrated circuit is analysed to save time and money. Unfortunately, returning for further analysis requires another sample.

It would be advantageous to provide a method of imaging an integrated circuit that does not have these and other limitations.

SUMMARY OF THE INVENTION

In accordance with the invention there is provided a method of imaging an integrated circuit comprising the steps of:

disposing the integrated circuit on a support for securing the integrated circuit in fixed relation to the support; and iterating the following steps until a predetermined portion of the integrated circuit is imaged:
using a focused ion beam imaging system for providing a focused ion beam, imaging a portion of an outer surface of the integrated circuit by capturing a plurality of images of different locations on the integrated circuit, relative motion between the support and the focused ion beam occurring between image capture operations, and,
etching a portion of the outer surface from the integrated circuit to expose material below the outer surface using an etching system, the etching performed with the integrated circuit secured in fixed relation to the support.

In an embodiment the method comprises the step of extracting circuit information from the composite image absent a step of processing the composite image to extract foreground information from background information.

In an embodiment the method comprises the steps of filtering the composite image to perform one of reducing noise and sharpening edges; and, extracting circuit information from the composite image, absent a step of processing and/or filtering the composite image to extract foreground information from background information.

In accordance with another embodiment of the invention, there is provided a method of imaging an integrated circuit comprising the steps of:

disposing the integrated circuit on a support for securing the integrated circuit in fixed relation to the support;

automatically iterating the following steps until a predetermined portion of an integrated circuit is imaged:
using a focused ion beam system for directing a focused ion beam, capturing an image of a first layer of the integrated circuit and providing a first signal based on the captured images;
then providing relative motion between the support and the focused ion beam the relative motion provided with the integrated circuit secured in fixed relation to the support; and
storing data relating to the captured image and based on the first signal.

In accordance with the invention there is also provided a method of imaging an integrated circuit comprising the steps of:

disposing the integrated circuit on a support for securing the integrated circuit in fixed relation to the support;

iterating the following steps until a predetermined portion of an integrated circuit is imaged:

using a focused ion beam imaging device for providing a beam, capturing a plurality of images of the integrated circuit from a same relative location between the support and the beam, etching of the imaged location of the integrated circuit performed between image capture operations, the etching performed with the integrated circuit secured in fixed relation to the support; and, providing relative motion between the support and the beam.

BRIEF DESCRIPTION OF THE DRAWINGS

An exemplary embodiment of the invention will now be discussed in conjunction with the attached drawings in which.

DETAILED DESCRIPTION OF THE INVENTION

Examining and understanding integrated circuits has numerous applications. Designers often review integrated circuit components of competitive manufacturers in order to improve their designs; in patent infringement actions, an explanation of an ICs circuitry and mode of operation is sometimes required; and, in reverse engineering—copying functionality—of an integrated circuit component, years can be eliminated from a design cycle. Current practices, though often significantly faster than an entire engineering redesign, are tedious and require significant levels of skill.

In this disclosure and the claims that follow, the following terms are used as defined here. Plan-view refers to a top-view; a plan view is a view of substantially a single layer of an integrated circuit and not a cross section view of an integrated circuit. Circuit information refers to information relating to a circuit contained on the integrated circuit. Some examples of circuit information include layout information, circuit components, circuit interconnects, schematics, netlists, circuit redundancy, etc. The phrase "improve imaging results" refers to improving the results of an imaging step for use in a further step of analysis. The improvement resulting in an image, which are preferred for analysis of circuit information contained within the image.

Figure 1:
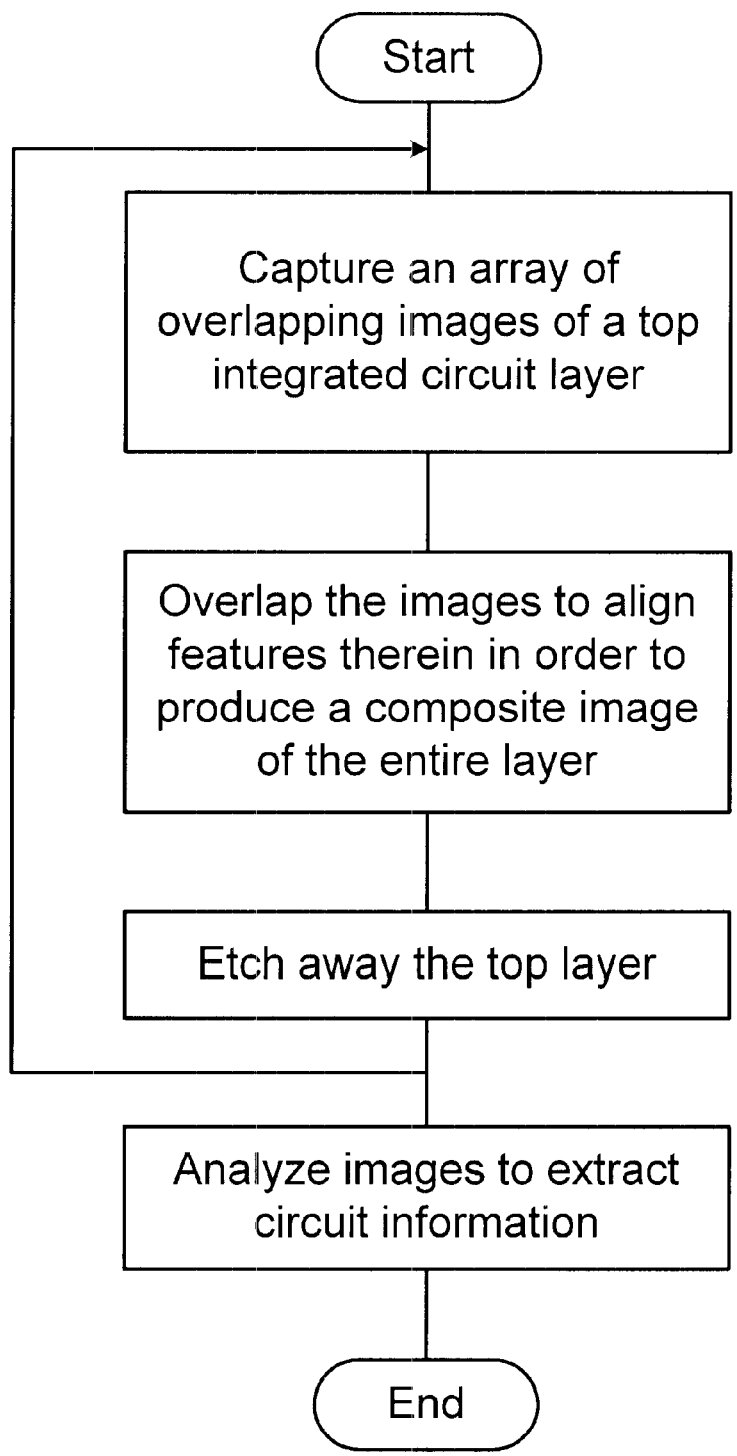
FIG. 1 is a simplified flow diagram of a method according to the prior art of imaging an IC using mosaicing.

Referring to FIG. 1, a simplified block diagram of prior art reverse engineering processes is shown. An imager is used to image a layer of an IC. Unfortunately, because of the detail contained in a single IC layer, the imager is capable of imaging only a small section of a layer at a time. Further, due to the spacing of traces within an IC imaging systems can not image abutting images accurately. A stage is provided for moving the IC relative to the imager. A plurality of overlapping images is captured in order to ensure that every aspect of the IC layer is imaged.

The captured images are then assembled at an assembly station. An assembly station often comprises a large table where the images are laid out and aligned by hand. Alternatively, current trends toward computer aided design propose that a computer algorithm be used to align images and mosaic them into a single final composite image of a layer. The composite image is then stored for further analysis. Unfortunately, due to the large amount of redundancy in a typical IC, many images are very similar. Further, due to the limited information contained within each image frame, automatic alignment of images is very difficult. A detailed review of the images and their alignment is used to identify mistakes in automatic alignment prior to analysing the composite image formed.

One common solution proposed in the literature is to provide electronic images on a computer and to align these manually aided by image processing algorithms of the computer system. Though significant performance improvements are realised, the system is not as desirable as one that is truly automated.

Once a layer is imaged, the IC is removed from the imaging station and moved to an etching station. At the etching station, a layer of material is removed from the IC to expose another layer of circuitry. The IC is then returned to the imaging station for imaging of this other layer. Since current IC tolerances are less than a micron, it is near impossible to ensure accurate placement and alignment of the IC with each insertion into the imaging station. Therefore, a composite image alignment station is required. At the composite image alignment station, the composite images are stacked together and features on adjacent layers are identified by hand in order to determine inter layer connections and inter layer alignment. The resulting three-dimensional composite image is analysed to determine a schematic or other representation of the circuitry.

Because the composite images may contain errors of alignment, the alignment of composite images to form the three-dimensional composite image may also contain errors in alignment—the errors propagating. It is desirable to limit alignment errors in initial stages in order to improve overall alignment.

As is evident to those of skill in the art, the above-described method requires days or weeks of highly skilled effort. The imaging and etching process requires significant human intervention and the resulting data requires a significant amount of human assisted interpretation.

As traces on integrated circuits are miniaturised, the limitations of optical imaging using conventional microscopes are apparent. Current integrated circuit spacing is generally sufficiently large for optical imaging; this will likely be untrue in a few years.

Throughout the specification and the claims the term capturing an image or captured image refers to individual images captured by an image capture means. The term imaging is used in its general meaning and includes images captured using scanning electron microscopes, focused ion beam imaging devices, and other imaging or sensing devices which generate image or other sensed data arranged in an array corresponding to sensed locations.

Figure 2:
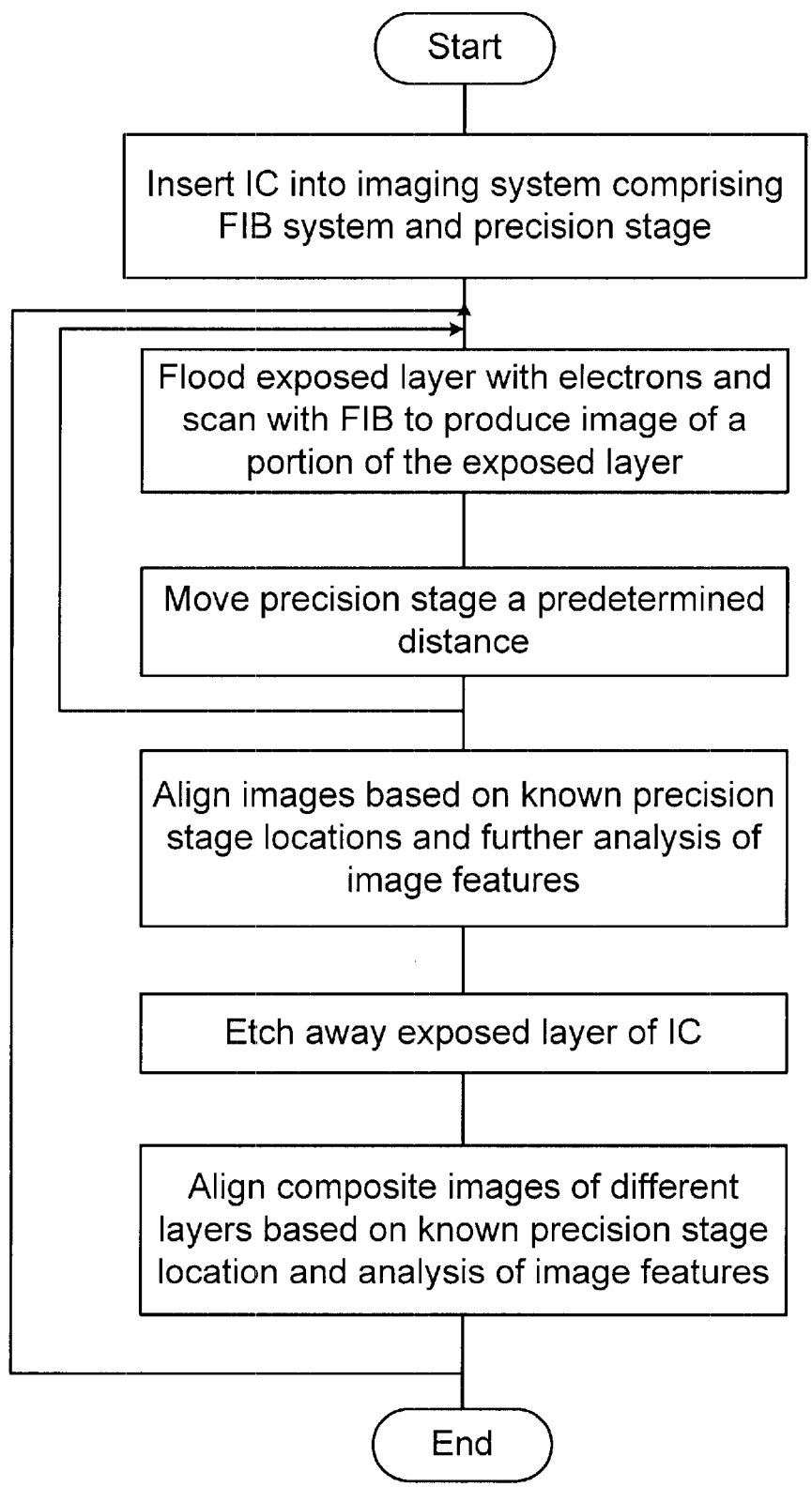
FIG. 2 is a simplified flow diagram of a method according to the invention of imaging an IC using mosaicing.

Referring to FIG. 2, a simplified flow diagram of a method according to the present invention is shown. An IC is inserted onto a precision stage for imaging by a focused ion beam (FIB) imaging device. Gallium ions are projected toward the IC surface. Upon impinging on the IC surface, both ions and electrons are sputtered off and electrons are emitted. Some of these sputtered particles are analysed in order to generate an image of the IC. In general, information generated based on analysis of ions which are sputtered from the surface provides images that are more spatially accurate. Rendering electrical charge on the surface of the IC uniform enhances this accuracy. A known method of accomplishing this is by flooding the surface with low energy electrons.

Preferably, the IC is prepared, having a first layer exposed for imaging. The IC is secured in place by securing means. Securing means for retaining ICs in place during imaging are well known and include gluing, mechanical clamping, etc.

A surface of an exposed layer for imaging is flooded with a low energy electron flow. As described above, these electrons help neutralise charge on insulated portions of the circuit and, thereby, improve image accuracy and alignment by reducing image drift. The FIB imaging device captures an image of a portion of the IC layer by analysing sputtered ions therefrom. Alternatively, two images are captured—one of sputtered ions while the low energy electron flow is active and one of sputtered electrons without a low energy electron flow. A precision stage upon which the IC is mounted is moved to allow capturing of another image. Preferably, stage precision is at least as accurate as minimal spacing within an IC. The use of an interferometric precision stage as is available in FIB systems commercially available from several FIB system manufacturers allows for such precision. Preferably precision is better than 50% of a smallest feature size to be imaged and processed. Preferably, captured images overlap a predetermined amount in order to provide a confirmation of stage accuracy. Further images of portions of the IC layer are captured until a mosaic of the entire layer can be constructed from the captured image data.

When a stage is accurate, image overlap is obviated and image alignment is known. Unfortunately, due to the precision of current ICs, a precision of better than 0.1 microns is required in an accurate stage in order to allow straightforward alignment based on stage positioning and image processing. Because of the redundant nature of integrated circuits, precision of better than ⅓ of trace spacing is required in order to provide a truly indicative estimate of alignment. Image processing is then capable of deterministically aligning the images. As is evident to those of skill in the art, at current rates of progress a stage having a precision of 0.1 microns is unlikely to remain sufficiently precise for a significant length of time. Because of this, it is advantageous to improve methods of image alignment in order to maintain current functionality with denser ICs without replacing an entire imaging system or precision stage.

Most precision stages are designed to provide precision in a single movement or a small group of movements with human operator control. For example, when an optical microscope precision stage is designed, its intended use is to allow navigation to a location where analysis is necessary. As such, during a single day, the stage is often only moved half a dozen times over medium length distances and a few more times over short distances. The heat generated is usually very little and the heat dissipates quickly once movement is stopped. When heat is generated, temperature rises.

An SEM imaging system uses electromagnetic lenses for focusing the beam. As such, a stable current is required for good imaging and beam stability. Temperature, because it affects resistance, affects current flow and affects image quality. An FIB imaging system relies on electrostatic lenses and, therefore, is less affected by changes in environmental temperature. For example, heat generated by stage motion and frequent movement has little effect on a FIB imaging system. Also, SEM imaging devices produce images that vary in rotation depending upon a ration of lens height to sample height. This is a result of beam rotation within the magnetic fields generated by the lenses. The electrostatic lenses of a FIB do not produce equivalent image rotations allowing for a simpler image-processing step for forming a composite image. Simpler processing steps save time and often increase reliability. Consequently, in reverse engineering applications, FIB imaging devices present some significant advantages.

Large depth of field (focus) of an FIB is well known. This large depth of field offers significant advantages over optical imaging systems in imaging of integrated circuits because a need to refocus the imaging system upon stage movement and image blurring due to different distances to the IC surface appearing in a same image frame are eliminated. An example of such a difference in distances might occur when imaging a transition between the memory array and the peripheral circuitry of a dynamic random access memory IC device.

The FIB imaging apparatus is used to etch away material from the exposed IC layer in a selective fashion. This allows for imaging of subsequent layers in an automated fashion without requiring removal and replacement of the IC. Using a precision stage, alignment between layers is known within the precision of the stage, because the IC has not been moved. Further, by etching only a portion of the exposed layer, accurate alignment between layers is ensured using a simple image correlation technique whether or not a precision stage is used.

Preferably, some analysis of image data is performed prior to etching away material. Advantageously, such a process is used to etch small quantities of material from portions of an image that are determined to require cleanup. Also, such a process allows etching of material in predetermined quantities to confirm analyses, increase data quantities, or perform testing. Because the entire imaging, analysis, and etching process is performed in situ with minimal or no operator assistance, etching small amounts of material wastes far less time than when performed using the prior art method of removing the IC, etching the IC, and then replacing the IC. Also, the additional data determined through "cleanup" etching improves results of the automatic analysis system and thereby reduces a need for human intervention or verification. These advantages and others are apparent to those of skill in the art from this disclosure.

Figure 3A:
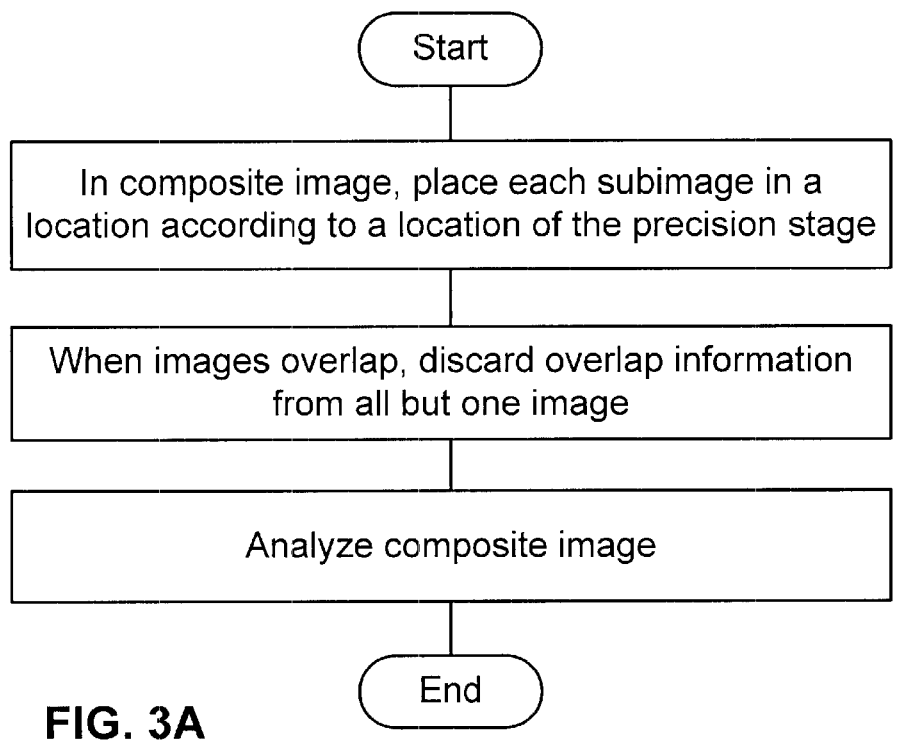
FIG. 3a is a simplified flow diagram of a method of mosaicing using location information provided by a precision stage.

Referring to FIG. 3a, the plurality of images are aligned and assembled to form a composite image of a layer of the IC. The assembly is performed as follows: each image is disposed at its known location as indicated by the precision stage, redundant image data in the form of overlapping image portions are discarded. The composite image is ready for further analysis. The assembly is performed automatically and requires no operator intervention. This is due to the fact that the precision stage allows for accurate alignment of even highly redundant circuits.

Figure 3B:
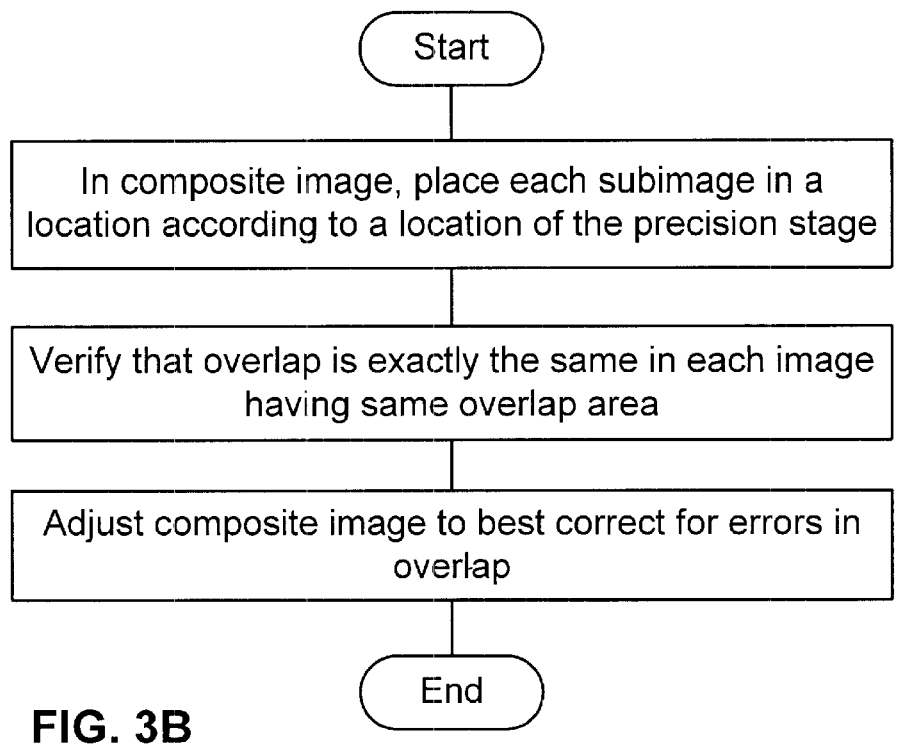
FIG. 3b is a simplified flow diagram of a method of mosaicing using location information provided by a precision stage and image correlation.

Referring to FIG. 3b, a method similar to that of FIG. 3a is shown wherein image analysis including correlation of overlapping image portions is performed to improve alignment beyond the precision of the precision stage. As indicated above, this method is preferred to that shown in FIG. 3a because it is applicable to systems having stages of lower precision relative to track spacing in the IC. Of course, optionally, a complete image mosaicing algorithm relying on precision stage information and image analysis is used for forming composite images. Such a mosaicing system will hopefully extend imaging system utility to smaller IC spacing than is currently available.

Figure 3C:
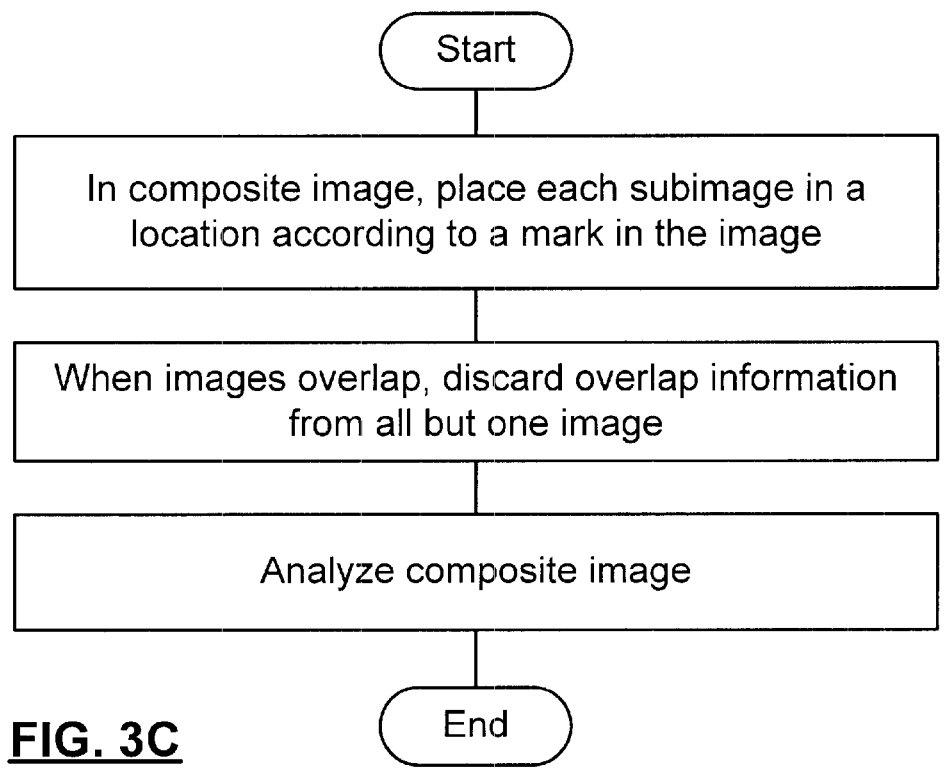
FIG. 3c is a simplified flow diagram of a method of mosaicing when using location information provided by precision markings on the IC.

Referring to FIG. 3c, the plurality of images is then assembled into a composite image of a layer of the IC. The images are each marked with a location. The marking is made on the IC itself to ensure correct alignment. Examples of markings include overlay patterns, banding, etched marks within each image, etc. The construction is performed as follows: each image is disposed at its known location as determined through analysis of the markings, redundant image data is discarded. The composite image is ready for further analysis. The assembly of the composite image is performed automatically and requires no operator intervention because the markings allows for accurate alignment of even highly redundant circuits.

For example, when image distortion is not considered a significant source of error, an image is captured, an alignment mark is etched at each corner of the image of a same portion of the integrated circuit. An image of a same portion of the integrated circuit is captured with the alignment marks. The stage is moved and another image, overlapping the first image and including at least one alignment mark and preferably two such marks is then captured. Another set of alignment marks is etched. It is apparent that in subsequent images only one or two such marks are required depending on how many marks is already present in the captured image. For the first image, three marks are required. It is evident how to apply such marks depending on an order of image locations imaged.

Since each image is captured with and without newly etched marks, no information is lost and marks are easily used to align captured images having no new marks to form a composite image absent marks. Of course, when marks do not interfere with analysis, only one image (with marks) is captured at each location. Since the marks are etched in situ, the marks are designed for ease of etching identification, and alignment. In order to etch using a focused ion beam device, the beam is maintained in a single location with a sufficient energy level to etch material from the integrated circuit surface. Etching in this manner is known.

Figure 3D:
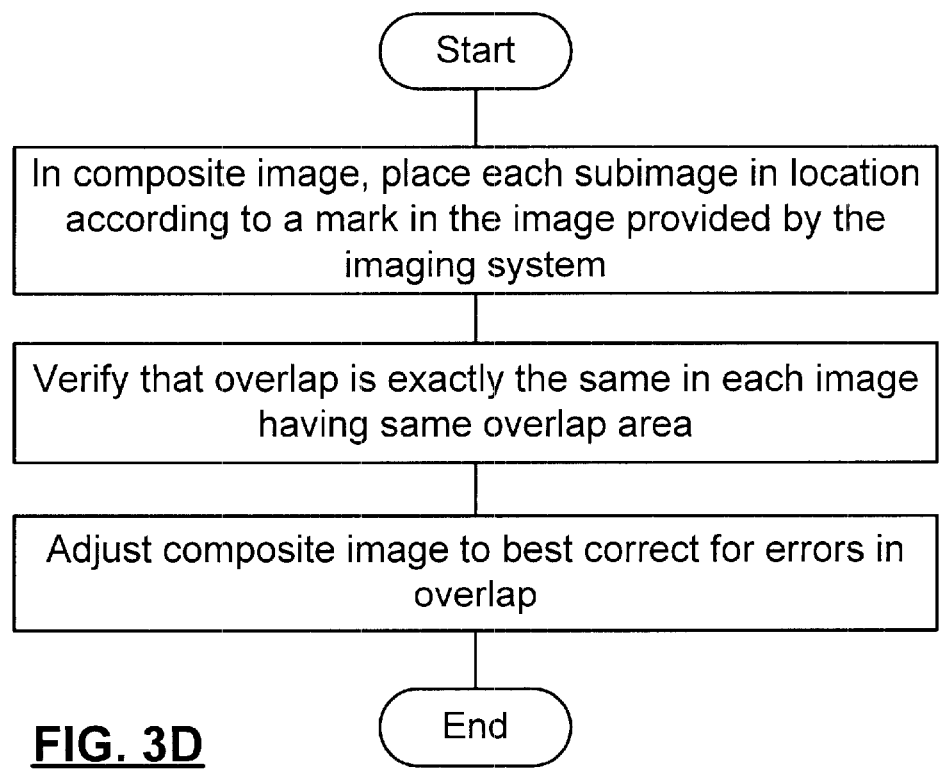
FIG. 3d is a simplified flow diagram of a method of mosaicing when using location information provided by precision markings on the IC and image correlation.

Referring to FIG. 3d, a method similar to that of FIG. 3c is shown wherein image analysis including correlation of overlapping image portions is performed to further improve alignment. Such a system is of particular importance when warp and distortion exist within images. Analysis of image overlap sections allows for reducing effects of distortion and warp within the composite image.

Figure 3E:
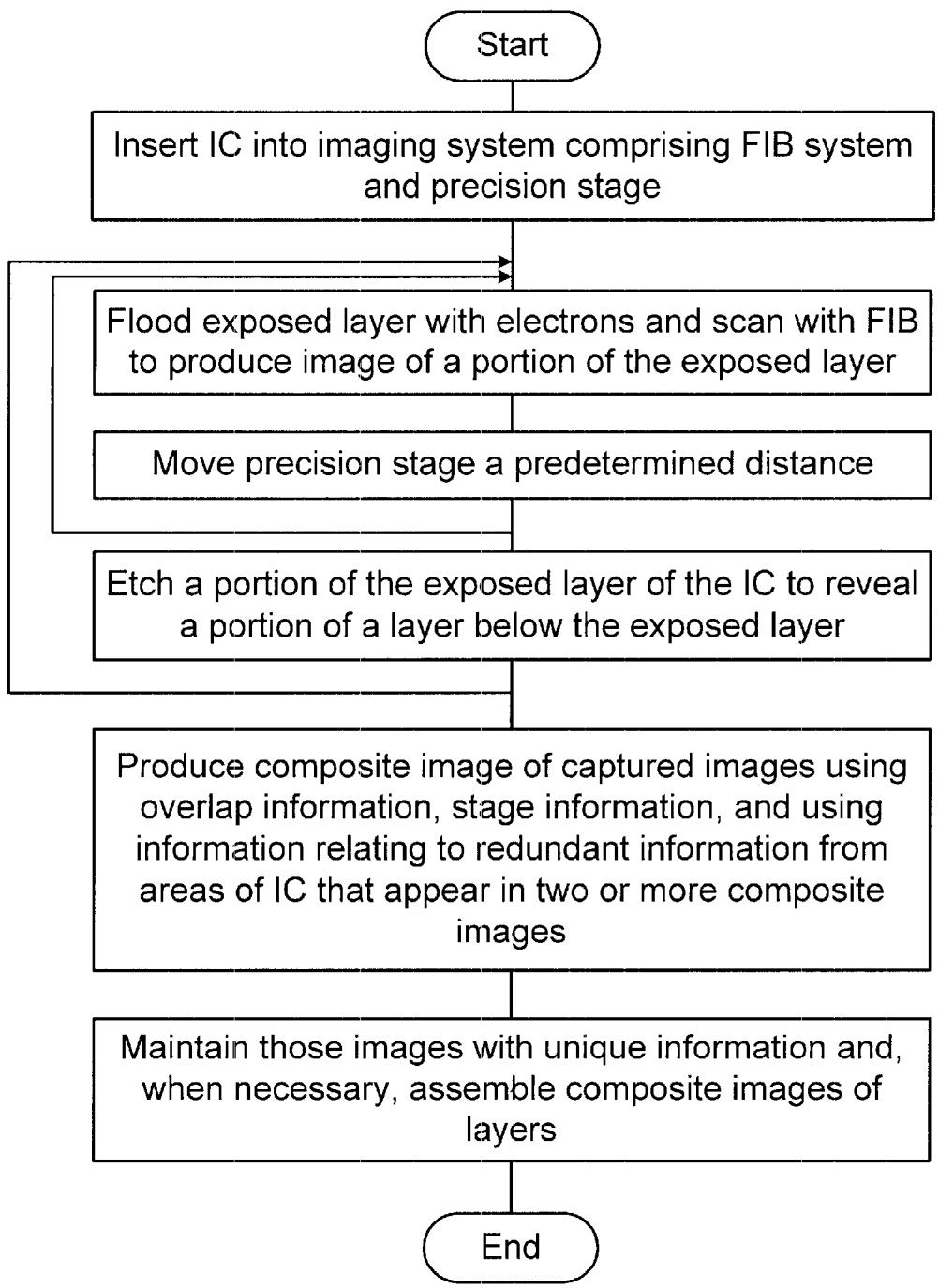
FIG. 3e is a simplified flow diagram of a method of imaging an IC using mosaicing wherein information is captured in a redundant fashion to facilitate composite image alignment and assembly.

For example, referring to FIG. 3e, a composite image of layer 1, the uppermost layer, is assembled. A substantial portion less than the whole of layer 1 is etched to reveal layer 2. A composite image of layer 2 and layer 1 as exposed is assembled. The remainder of layer 1 is etched to expose the entirety of layer 2. A composite image of layer 2 is assembled. It is evident to those of skill in the art that aligning layers 1 and 2 accurately is greatly facilitated through added correlation information between the composite images of layer 1 and layer 2 provided by the composite image of partial layer1/layer2. Analysis of traces between layers allows for increased accuracy of alignment. Even when layers contain substantially redundant information and large unused areas, alignment is likely accurate.

Applying the above method, the composite image of layer 1 is aligned with the composite image of layer 1/layer 2 by aligning the redundant information. The redundant information should align exactly and, when this is not the case, corrections are applied to the composite images. Once aligned, layer 1/layer 2 is aligned with layer 2. Again misalignments are corrected. When desirable, the process is iterated until no misalignment occurs. As is evident, since layer 1 and layer 1/layer 2 are aligned and layer 1/layer 2 and layer 2 are aligned, stacking them and removing the layer 1/layer2 from the middle results in an accurately aligned layer 1 and layer 2.

Alternatively, following a method according to FIG. 3e, the portion of layer 1 that is etched comprises a portion of each captured image. This provides increased information to allow for alignment of every image with an image of another layer. In use, such a method provides additional information for mosaicing and for aligning composite images. Since, composite image alignment is performed using many correlated locations, composite image skew, stretching, or misalignment result in errors in composite image alignment. When such errors occur, an error correction algorithm similar to that described above is employed to realign images within the composite image.

When a portion of each captured image contains layer 1 and layer 2 information in the images captured of layer 1/layer 2, the iterative correction and realignment algorithm disclosed above results in a "best" composite three-dimensional image of the IC. For a plurality of layers, each intermediate layer—layer n/layer n+1— provides alignment information for each captured image. Each image is aligned using image analysis to adjacent images and using the additional information of the intermediate layer. This results in a significant ability to correct skew, imaging errors caused by deflection, and other causes of misalignment.

Figure 4:
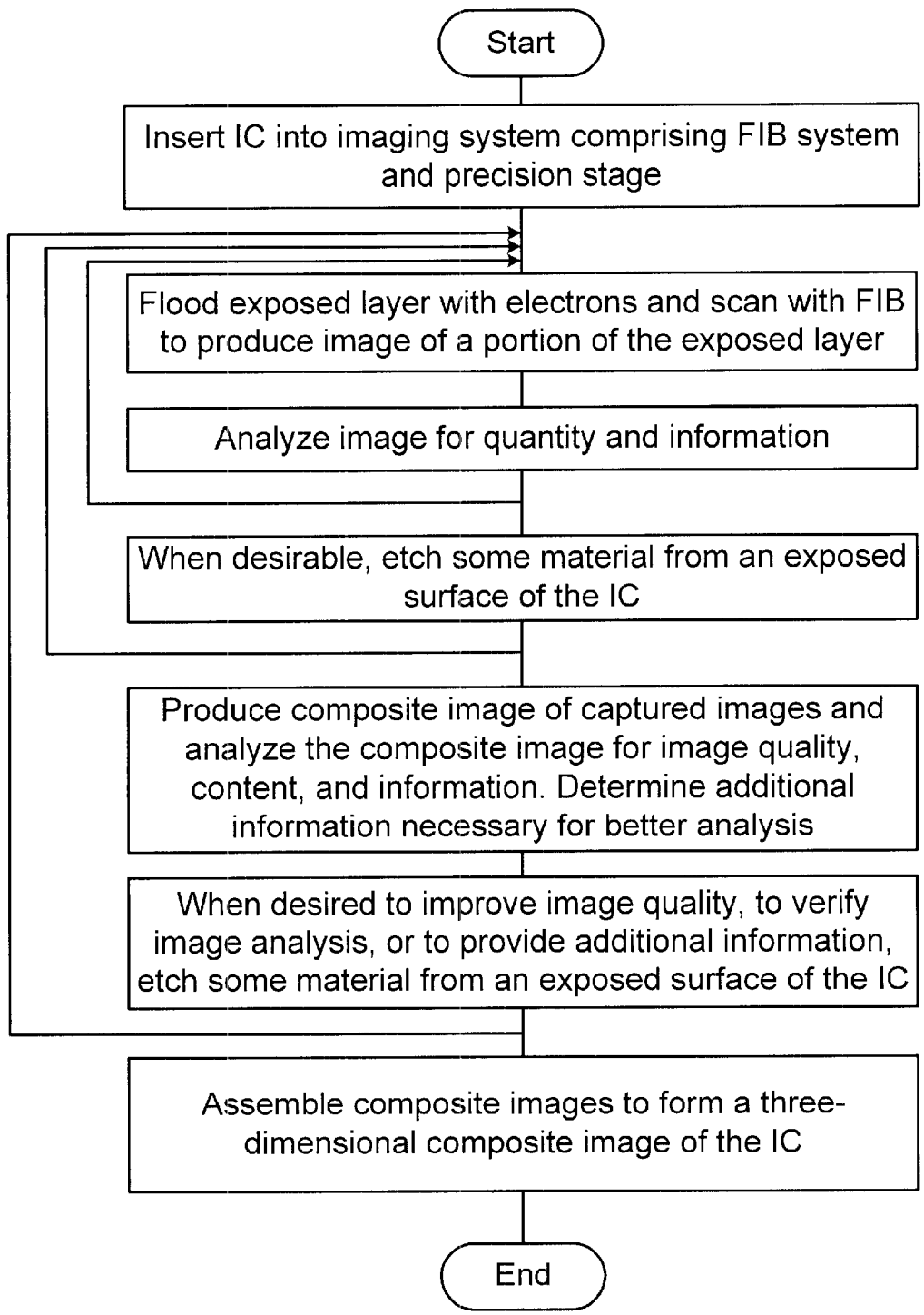
FIG. 4 is a simplified flow diagram of a method of imaging an IC using mosaicing wherein image information is analysed to determine required etching and to enhance image quality through etching and re-imaging when desirable.

Referring to FIG. 4, another method is shown outlining advantages of the present method. A composite image of layer 1, the uppermost layer, is assembled. The composite image is analysed. Those areas that are difficult to analyse are recorded, as are areas where information below the uppermost layer may be indicative of correct or incorrect analysis. Each recorded area is etched for improving the aforementioned analysis. Images are captured of the cleaned areas of the IC and are analysed to determine whether the newly captured images are of better quality than the previously captured images. A new composite image is assembled with those images having a better quality from the captured images. Those areas where etching is done to verify the analysis are imaged and the analyses are verified. When correct, the system increases its probability of having reached an accurate solution. When incorrect, the system attempts to resolve contradictions or records the possibility of the error and the location for later review by a further algorithm or by a human operator. Optionally, the method shown in FIG. 4 is performed iteratively until the analysis and the composite image are of a desired quality.

For example, when using a scanning electron microscope system, imaging to a predetermined depth occurs. When a contact occurs between metal 1 and metal 2, this is evident. When using a FIB system, imaging of an external surface is a straightforward task, but imaging to a depth beyond the surface is very limited. This is because ions are very much larger than electrons and, unlike electrons, do not penetrate through the closely spaced atomic layers. They are therefore stopped much nearer the surface. Upon analysing an image and determining the presence of a potential metal contact, etching and imaging of material below the contact allows for identification of the metal 1 as a contact with a lower layer or not. In some applications, identification of features and their function is the desired end result and, as such, the ability to gather additional information through analysis and partial etching of layers is significantly advantageous.

Figure 5:
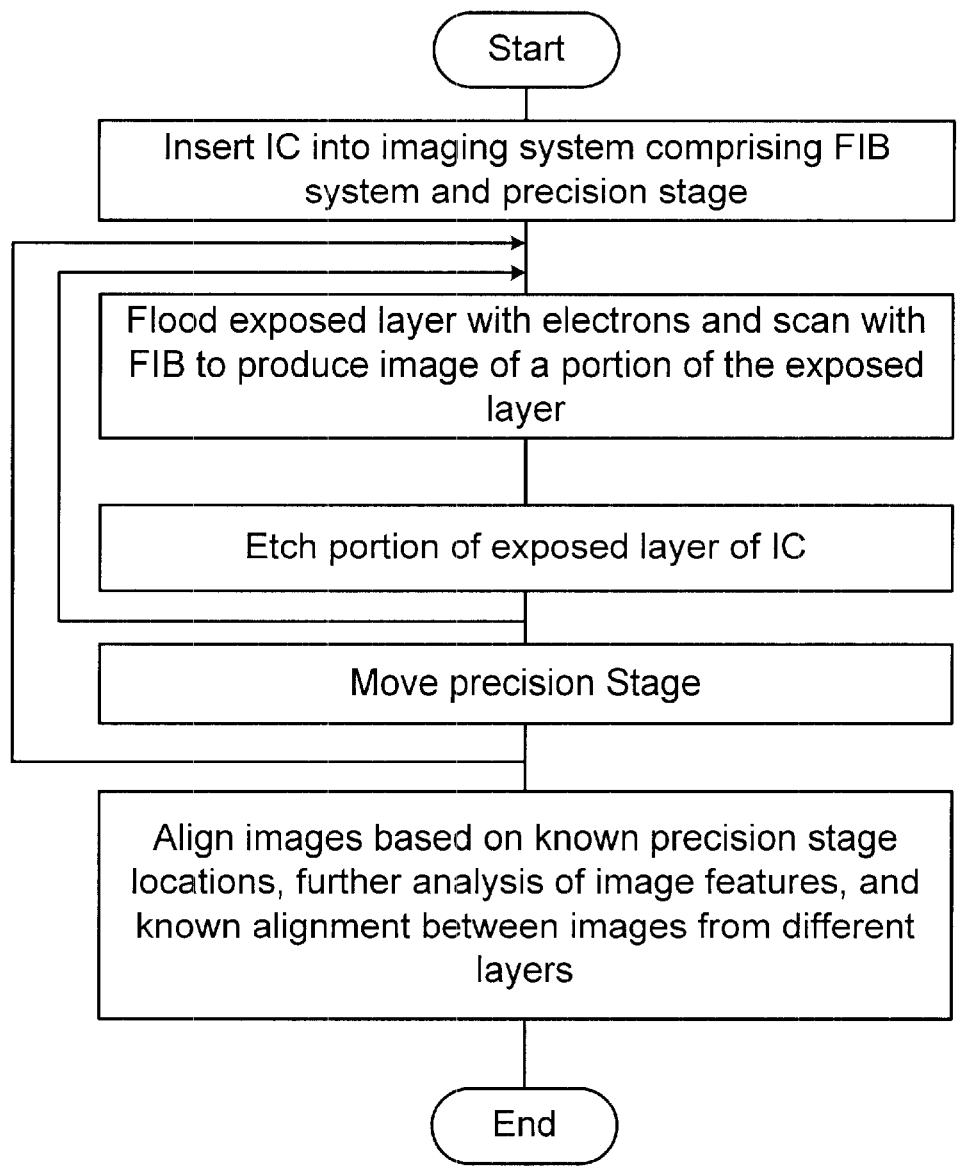
FIG. 5 is a simplified flow diagram of a method of imaging an IC using mosaicing wherein information is captured in a redundant fashion to facilitate composite image alignment and assembly.

Referring to FIG. 5, a method of mosaicing an entire multi-layered IC according to the invention is shown. A FIB is used to image one portion of the IC. A portion smaller than the imaged portion is then etched and a same portion is imaged. Alternatively, a portion having a same size is etched. The process is repeated for a plurality of layers. The precision stage is then moved for imaging the unetched portions. An image of another portion of the uppermost layer is captured. This process is repeated until the entire IC or a predetermined portion of the IC is imaged. During a processing step, alignment of captured images that are in stacked alignment (captured without moving the stage) is substantially known because the stage is not moved between imaging of multiple layers at a single location. Mosaicing of captured images on a same layer is accomplished in dependence upon the plurality of captured images of different layers having known spatial relations.

An analogy of alignment of images according to the method of FIG. 5 is simultaneous equations in mathematics. When an equation has two variables, it cannot be solved; another equation is needed. When two adjacent images are aligned, redundancy often results in an absence of a single solution. Each layer results in a number of potential solutions. By providing additional layers with known relations to existing layers or each other, in our analogy, more equations are added to the system. Selecting only potential solutions that are substantially common to all layers, a small number of potential solutions remain likely. This number is often one but need not be so. Even when the solution is not one, other information such as stage precision, even when using a non-precision stage, allows for discrimination of a correct solution. Of course, a precision stage increases likelihood of correct alignment.

As noted above, as IC trace spacing is decreased, precision stages and imaging tools become obsolete. The method of FIG. 5 allows for significant extension of a useful life of a precision stage by increasing alignment information.

Figure 6:
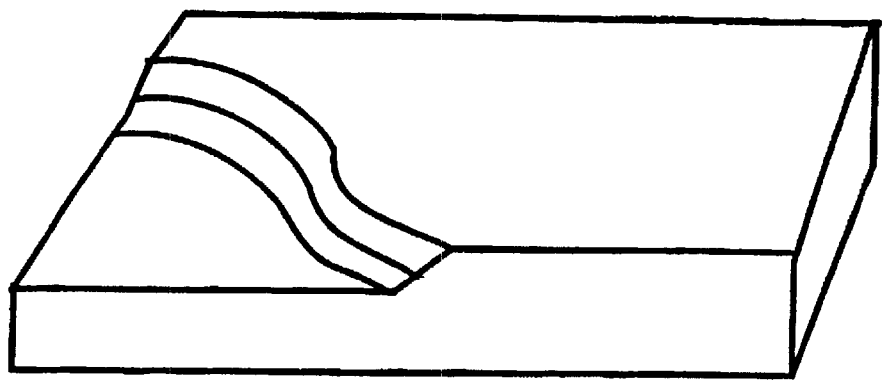
FIG. 6 is a simplified diagram of an IC with part of each of two layers etched away; and, FIG. 7 is a simplified diagram of 4 images—two from each of two layers—for alignment to form composite images.
Figure 7A:
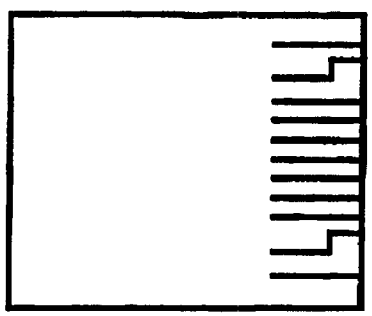
Figure 7B:
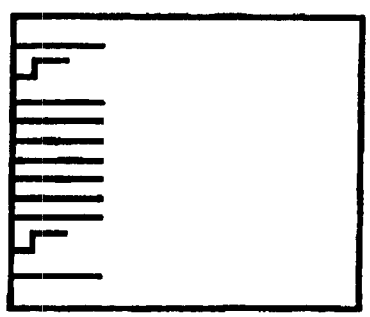
Figure 7C:
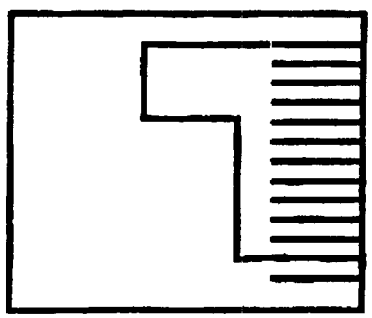
Figure 7D:
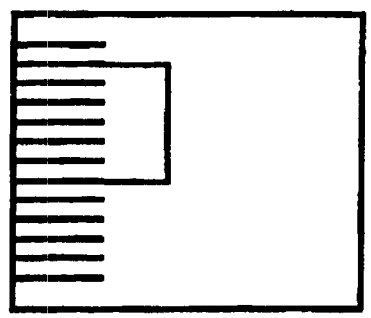

Referring to FIG. 6, a simplified diagram of an IC being imaged is shown. Two layers are partially etched and a third is being imaged. The images captured using such a process are then aligned. The alignment process is explained with reference to FIG. 7. Four images are shown in FIG. 7. The upper two images, a and b, are from an uppermost layer. The lower two images, c and d, are from a lower layer. The images were captured according to the method of FIG. 5. The images of layers c and d are difficult to align because lines on those layers are parallel and disposed perpendicular to the break between images. That said, the images a and b are easily aligned due to spaces between parallel lines. Therefore, layers c and d are aligned because an origin of layer c corresponds to a spatial location of an origin of layer a and an origin of layer d corresponds spatially to an origin of layer b.

As is well known, gas assisted etching requires selection of an appropriate gas. Often, it is desirable to select a gas providing a very fast etching rate on certain materials and a relatively slow etching rate on other materials in order to slow the etching upon transition to another layer. The selection of gases for this procedure is usually performed by FIB operators or other skilled individuals. According to an embodiment of the invention, an image is analysed to determine a gas for use in gas assisted etching. The gas is selected based on image contrast and identifiable features within the image. For example, metal identified within an image is indicative of a metallized layer and an appropriate gas is used. The selection of gases based on chemical content is according to known gas assisted etching applications. Alternatively, etching the integrated circuit then tests the selected gas and verification through imaging or measuring is used to determine etch rate. When the etch rate is insufficient, another gas is used and so forth until an appropriate gas is selected. Of course, the selection of appropriate gases for such a system and image features indicative of a first selected gas or an order of selection for the gases is easily determined through experimentation.

It is evident to those of skill in the art that aligning images to form composite images of IC layers, analysing images to determine a necessity of cleaning up an uppermost layer of an IC being imaged, evaluation of analysis, aligning composite images of different layers, and other steps commonly performed by operators of reverse engineering equipment require significant time and effort. As a direct result, an IC may remain at an imaging station for a prolonged period of time and simultaneously, imaging thereof may occupy an experienced reverse engineer's time for a same period or longer. According to the prior art, performing all imaging prior to performing operator-assisted tasks results in less effective imaging and potentially in loss of information. It is therefore undesirable.

According to the present invention, these steps are provided automatically without significant operator assistance. Preferably, an IC is inserted into an FIB system according to the invention and is checked periodically to ensure correct operation. Incorrect operation results, for example, from empty gas supplies when gas assisted etching is used, when unresolved errors of significance arise, etc. Other than those situations requiring operator assistance, the imaging and composite three-dimensional image assembly is conducted unassisted. This reduces human resource requirements and improves efficiency. Also, the automated FIB system is capable of operating for a considerable number of hours more than human engineers over a same period of time.

Further according to the invention, a step of processing to extract foreground data corresponding to an uppermost layer of an integrated circuit from background data is obviated. Because a FIB imaging system does not penetrate a sample being imaged, resulting images comprises substantially foreground data. Optionally, filtering to remove noise and to sharpen edges between features within images is performed. Processing of image data is well known in the art of machine vision and it is straightforward for one of skill in the art to apply methods of filtering or other processing methods for image enhancement to the present application.

Also, according to the invention, extracted circuit component information is stored with component location within the integrated circuit in order to permit association of circuit components with IC areas—regions—in order to provide schematics that are easily associated with the layout. Because circuit layout is often functionally based, this often permits reconstruction of schematics into blocks of functionally associated circuit elements in a fully automated fashion. It has been found that schematic generation according to layout and circuit information results in schematics that are more easily read. Further, readability is enhanced by establishing a number of interconnects between schematic pages and substantially minimising said number according to any of a number of algorithms. One such algorithm is a brute force approach to select a schematic pagination that reduces inter-page connections.

The use of a FIB imaging system permits image enhancement through physical modification of the integrated circuit by etching during imaging thereof. Prior art systems and methods do not disclose such an advantage, which is significant because of increased efficiency through reduced operator involvement.

Numerous other embodiments are envisioned without departing from the scope or spirit of the present invention.

What is claimed is:

1. A method of imaging an integrated circuit comprising the steps of:
    disposing the integrated circuit on a support for securing the integrated circuit in fixed relation to the support;
    iterating the following steps until a predetermined portion of the integrated circuit is imaged;
    using a focused ion beam imaging system for providing a focused ion beam, imaging a portion of an outer surface of the integrated circuit by capturing a plurality of images of different locations on the integrated circuit, relative motion between the support and the focused ion beam in a direction parallel to the plane of the image occurring between image capture operations, and,
    etching a portion of the outer surface from the integrated circuit to expose material below the outer surface using an etching system to provide image markers, the etching being performed with the integrated circuit secured in fixed relation to the support; and, forming a composite image of an imaged outer surface of the integrated circuit in which the images of different locations partially overlap one another, and a composite image of the outer surface is formed in dependence upon the image marker locations and orientations.

2. A method of imaging an integrated circuit as defined in claim 1 wherein the step of etching exposes material below the outer surface for exposing a different outer surface.

3. A method of imaging an integrated circuit as defined in claim 1 comprising the step of extracting circuit information from the composite image absent a step of processing the composite image to extract foreground information from background information.

4. A method of imaging an integrated circuit as defined in claim 3 wherein circuit information includes location based information for use in schematic generation according to layout.

5. A method of imaging an integrated circuit as defined in claim 1 comprising:
    processing the composite image to perform at least one of reducing noise and sharpening edges; and,
    extracting circuit information from the composite image, absent a step of processing the composite image to extract foreground information from background information.

6. A method of imaging an integrated circuit as defined in claim 1 comprising the step of extracting circuit information from the composite image of the outer surface absent a step of processing the composite image to extract foreground information from background information.

7. A method of imaging an integrated circuit as defined in claim 6 wherein circuit information includes location based information for use in schematic generation according to layout.

8. A method of imaging an integrated circuit as defined in claim 1 comprising the steps of:
    processing the composite image to perform one of reducing noise and sharpening edges; and,
    extracting circuit information from the composite image, absent a step of processing the composite image to extract foreground information from background information.

9. A method of imaging an integrated circuit as defined in claim 1 wherein the iterated steps are performed automatically.

10. A method of imaging an integrated circuit as defined in claim 1, wherein etching system is a gas assisted focused ion beam etching system.

11. A method of imaging an integrated circuit as defined in claim 1 comprising the step of analysing an image from the plurality of images to determine a gas for use in gas assisted etching.

12. A method of imaging an integrated circuit as defined in claim 1, wherein during the step of imaging, ions and electrons sputtered from the outer surface are analysed for imaging the portion of the outer surface.

13. A method of imaging an integrated circuit as defined in claim 1, comprising the steps of analysing an image of an etched portion of the outer surface from the integrated circuit to determine locations within the image requiring further etching; and,
    in dependence upon the analysis, performing further etching to improve imaging results.

14. A method of imaging an integrated circuit comprising the steps of:
    disposing the integrated circuit on a support for securing the integrated circuit in fixed relation to the support;
    automatically iterating the following steps until a predetermined portion of an integrated circuit is imaged;
    using a focused ion beam system for directing a focused ion beam, capturing an image of a first layer of the integrated circuit and providing a first signal based on the captured images;
    then providing relative motion between the support and the focused ion beam in a direction parallel to the plane of the image using a precision stage allowing accurate mosaicing of captured images, the stage being accurate to within 50% of the distance across a smallest feature size of the integrated circuit technology used in manufacture, the relative motion provided with the integrated circuit secured in fixed relation to the support; and
    storing data relating to the captured image and based on the first signal; and, forming a composite image of the first layer of the integrated circuit.

15. A method of imaging an integrated circuit as defined in claim 14 comprising the step of extracting circuit information from the composite image of the first layer absent a step of processing the composite image to extract foreground information from background information.

16. A method of imaging an integrated circuit as defined in claim 15 wherein the step of capturing images of a first layer comprises capturing plan view images of the first layer.

17. A method of imaging an integrated circuit as defined in claim 15 wherein circuit information includes location based information for use in schematic generation according to layout.

18. A method of imaging an integrated circuit as defined in claim 14 comprising the steps of:

processing the composite image to perform at least one of reducing noise and sharpening edges; and, extracting circuit information from the composite image of the first layer absent a step of processing the composite image to extract foreground information from background information.

19. A method of imaging an integrated circuit as defined in claim 18 wherein schematic information includes location based information for use in schematic generation according to layout.

20. A method of imaging an integrated circuit as defined in claim 14 wherein the step of providing relative motion is performed using a precision stage allowing accurate mosaicing of captured images absent a step of aligning image features.

21. A method of imaging an integrated circuit as defined in claim 14, comprising the step of performing gas assisted etching using the focused ion beam system.

22. A method of imaging an integrated circuit as defined in claim 14, wherein during the step of imaging, ions and electrons sputtered from the first layer are analysed to provide an analysis signal and wherein the first signal is based on the analysis signal.

23. A method of imaging an integrated circuit as defined in claim 14, comprising the steps of analysing an image to determine locations within the image requiring etching to improve imaging results; and, in dependence upon the analysis, using the focused ion beam system, performing etching to improve imaging results.

* * * * *